United States Patent [19]

Soloway et al.

[11] 4,024,161

[45] May 17, 1977

[54] 2-(2-HALO-1-(UNSATURATED ALIPHATIC))-5-NITROFURANS

[75] Inventors: Samuel B. Soloway; George Bernson Payne, both of Modesto, Calif.

[73] Assignee: Shell Oil Company, Houston, Tex.

[22] Filed: May 28, 1974

[21] Appl. No.: 473,653

[52] U.S. Cl. .......................... 260/346.1 R; 424/285
[51] Int. Cl.² ..................................... C07D 307/70
[58] Field of Search .......................... 260/346.1 R

[56] References Cited

UNITED STATES PATENTS

| | | |
|---|---|---|
| 3,225,106 | 12/1965 | Rabinowitz .................. 260/346.1 |
| 3,238,093 | 3/1966 | Ratts ............................. 424/349 |

*Primary Examiner*—Henry R. Jiles
*Assistant Examiner*—Bernard Dentz

[57] ABSTRACT

Certain 2-(2-halo-1-(unsaturated aliphatic))-5-nitrofurans, having activity with respect to microorganisms.

6 Claims, No Drawings

2-(2-HALO-1-(UNSATURATED ALIPHATIC))-5-NITROFURANS

DESCRIPTION OF THE INVENTION

It has been found that certain furans, characterized by substitution at the 2-position by a 2-halo-1-(unsaturated aliphatic)moiety and at the 5-position by a nitro moiety are active with respect to such microorganisms as fungi, bacteria, yeasts and molds. These furans also have been found to be active with respect to nematodes.

These furans can be described by the general formula

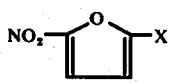

wherein X is

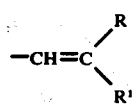

or is $-C \equiv C-R$, R is middle halogen (i.e. chlorine or bromine) and $R^1$ is middle halogen or is methyl.

These furans wherein R and $R^1$ differ can exist as stereoisomers. This invention includes all forms of the compounds and mixtures thereof.

These furans can be prepared by the methods described in the following examples. For each example, the identity of the product was confirmed by elemental analysis and by infrared and nuclear magnetic resonance spectral analyses.

EXAMPLE 1

2-(2,2-dichlorovinyl)-5-nitrofuran (1)

To a stirred mixture of 14.1 g of 5-nitro-2-furaldehyde and 22.1 g of dichloroacetyl chloride in 300 ml of benzene was added dropwise at 25°–30° over a 30-minute period a solution of 15.2 g of triethylamine in 50 ml of benzene. The mixture then was stirred at 25°–30° for an additional 30 minutes and then for 90 minutes at reflux. After cooling, the mixture was filtered and the filtrate was washed and dried, concentrated under reduced pressure and Claisen distilled to give a liquid product, b.p.: 88°–98° at 0.3 torr. (mainly 90°–95°). This material was crystallized from acetone/petroleum ether to give 1 as a light yellow solid, m.p.: 74°–75°.

EXAMPLE 2

2-(2,2-dibromovinyl)-5-nitrofuran (2)

To a stirred suspension of 6.5 g of zinc dust in 300 ml of methylene chloride was added, successively, 26.2 g of triphenylphosphine and 33.2 g of carbon tetrabromide. A mildly exothermic reaction carried the temperature of the mixture to 35°–40°, no cooling being applied. The mixture then was stirred for one hour at room temperature, then cooled to 15° and treated with 10.7 g of 5-nitro-2-furaldehyde. The mixture then was stirred overnight at 25° and filtered to remove suspended salt. The filtrate was concentrated under reduced pressure and the residue was extracted with two 200 ml portions of ether. The combined ether extracts were concentrated to a volume of about 100 ml, diluted with an equal volume of pentane, and cooled. Filtration gave triphenylphosphine oxide. The filtrate was concentrated under reduced pressure and the residue was recrystallized from either/pentane (1:2) to give a solid, m.p.: 73°–78°. Recrystallization of the solid from either/pentane (1:4) gave 2 as yellow prisms, m.p.: 76°–78°.

EXAMPLE 3

2-(2-chloro-1-propenyl)-5-nitrofuran (3)

To a solution of 9 g of 5-nitro-2-furaldehyde and 11.0 g of 2-chloropropionyl chloride in 100 ml of benzene was added dropwise at 25°–30° over a 20-minute period a solution of 10 g of triethylamine in 30 ml of benzene. After an additional 40 minutes, the mixture was stirred at reflux for 1.5 hours. The cooled mixture was washed with water, dried and concentrated under reduced pressure to leave a residue which was distilled to give a liquid product, b.p.: 92°–100° at 0.15 torr. This product was triturated with n-hexane to give 3 as a mixture of stereoisomers, a tan solid, m.p.: 55°–65°.

The bromo analog can be prepared by the same general procedure.

EXAMPLE 4

2-(2-chloroethynyl)-5-nitrofuran (4)

To a stirred solution of 20.8 g of 1 in 100 ml of dry tert-butanol was added dropwise at 5°–10° over a 30-minute period a solution of 11.2 g of potassium tert-butoxide in 100 ml of tert-butanol. The mixture then was stirred at 5°–10° for 1 hour longer. Concentration of the mixture under reduced pressure gave a dark residue which was extracted with ether and water. The ether phase was separated, dried over magnesium sulfate and Claisen distilled to give 4 as a liquid, b.p.: 73°–76° at 0.2 torr which solidified on standing, the solid having a melting point of 38°–41°.

The compounds of this invention have shown activity with respect to a number of typical classes of microorganisms including gram positive, gram negative and acid-fast bacteria, yeasts, fungi and mold organisms.

The activity of the compounds of this invention with respect to various classes of microorganisms was ascertained as follows:

The compound to be tested was suspended or dissolved in acetone to form a concentrated solution. The final "use" concentrations were prepared by appropriate dilution of this concentrated solution. The stock solutions were added to trypticase soy broth in culture tubes. The final concentration of acetone was kept to 1 percent or less to avoid any adverse effects on the organisms. The culture tubes containing the media and chemical dilutions were then seeded with the various test organisms. Following an incubation period of 24 hours for the bacteria and 72 hours for the fungi, observations were made on the presence or absence of growth of the organisms. The figures given in Tables I and II are the lowest dilutions in parts per million which prevented the growth of the test organisms.

Table I

| Organism | Growth Inhibition Endpoints (ppm) for Indicated Compound | | | |
|---|---|---|---|---|
| | Compound 1 | 2 | 3 | 4 |
| *Bacillus substilis* | 1–10 | 1 | 1–10 | |
| *Escherichia coli* | 1–10 | 1–10 | 1–10 | 1–10 |

Table I-continued

| | Growth Inhibition Endpoints (ppm) for Indicated Compound | | | |
|---|---|---|---|---|
| Organism Compound | 1 | 2 | 3 | 4 |
| Mycobacterium avium | 1-10 | 1-10 | 10-100 | 1-10 |
| Saccharomyces cerivisiae | 1-10 | 1-10 | 10-100 | 1-10 |
| Trichophyton mentagrophytes | 10-100 | | 10-100 | |
| Aspergillus niger | 1-10 | 1 | 1-10 | 1-10 |
| Dendron sp. | 1-10 | | | |
| Pyronellae sp. | 1-10 | | | |
| Macrosporium sp. | 1-10 | | | |
| Agrobacterium tumefasciens | 10-100 | | 10-100 | |
| Erwinia amylovora | 10 | | 10-100 | |

These microorganisms were selected because they are representative of different classes of microorganisms:

B. subtilis—gram positive bacterium
E. coli—gram negative bacterium
M. avium—acid-fast bacterium
S. cerevisiae—yeast
T. mentagrophytes—fungus
A. niger—mold (fungus)
D. sp.; P. sp.; M. sp.—organisms isolated from mold in shower stalls
A. tumefasciens—bacterium—causal organism of crown gall
E. amylovora—bacterium—causal organism of fire blight of pears and apples Compounds of the invention also were tested with respect to other microorganisms by the same test procedure with the following results:

Table II

| | Growth Inhibition Endpoints (ppm) for Indicated Compound | | | |
|---|---|---|---|---|
| | Compound | | | |
| Organism | 1 | 2 | 3 | 4 |
| Salmonella choleraesuis | 1-10 | 10-100 | | 1-10 |
| Staphyloccus aureus | 1-10 | 1-10 | | |
| Streptococcus fecalis | ~100 | ~100 | | |
| Enterobacter aerogenes ATCC 8329 | 10-100 | 10-100 | | |
| Trichoderma sp. ATCC 9645 | 10 | 1-10 | | |
| Verticillium albo-atrum | < 100 | | 1-10 | |
| Fusarium sp. | < 100 | | 10-100 | |

S. choleraesuis and E. aerogenes are gram negative bacteria. S. aureus and S. fecalis are gram positive bacteria. The Trichoderma species is a fungus. V. albo-atrum is a fungus which causes a vascular wilt in plants. The Fusarium species is a fungus which causes diseases in plants.

Thus, the microbiological activity of the compounds of this invention make them particularly effective for a variety of uses, including their use as anti-mold additives for paints, to prevent development of slime and algae in industrial water, to prevent slime in cutting oils and as general purpose germicides, antiseptics, disinfectants and sanitizing agents. The compounds appear to be relatively non-toxic orally and when applied to the skin of an animal. They are, thus, safe to apply and use taking only ordinary precautions to prevent them from harming the person applying them. They accordingly can be included in household cleaners, soaps and detergents to impart microbiocidal properties thereto.

Further, the compounds of this invention are somewhat volatile and the vapors control microorganisms on surfaces which the vapors contact. These compounds thus may be used as fumigants, or in slow-release formulations, for controlling molds in shower stalls, preventing mildew in closed containers, closets and the like.

The microbiocides of this invention are most effectively applied as a formulation in a solvent or solid or liquid carrier or diluent. Suitable liquid solvents or carriers include water, alcohols, ketones, aliphatic and aromatic hydrocarbons and the like. Suitable surface-active agents for suspending or emulsifying the microbicide with the liquid carrier may also be included. Suitable solid carriers include talc, bentonite, kieselguhrs, and the like.

The concentration of the furan necessary for inhibiting the growth of microorganisms will vary with the particular furan used, the type of microorganism, whether a carrier is included or not, environmental conditions, etc. Those skilled in the art can readily determine the suitable concentration for the particular application however—e.g., by the use of controls. When the furan is admixed with a carrier, the concentration of the furan in the formulation usually will range from about 0.001 to 95% by weight of the formulation. In dilute formulation applied for control of microorganisms, the concentration of furan in the formulation usually will range from about 10 to about 1000 ppm, and preferably from about 10 to about 100 parts per million of their weight of the formulation.

The invention claimed is:
1. A compound of the formula

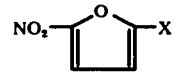

wherein X is

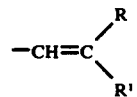

or —C ≡ C—R, R is middle halogen and $R^1$ is methyl or middle halogen.

2. A compound according to claim 1 wherein X is

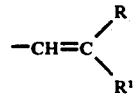

and R and $R^1$ each is chlorine.

3. A compound according to claim 1 wherein X is

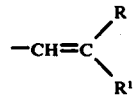

and R and $R^1$ each is bromine.

4. A compound according to claim 1 wherein X is

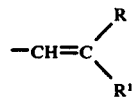

and $R^1$ is methyl.

5. A compound according to claim 4 wherein R is chlorine.

6. A compound according to claim 1 wherein X is —C ≡ C—R and R is chlorine.

* * * * *